United States Patent
Robertson et al.

(10) Patent No.: US 10,323,014 B2
(45) Date of Patent: Jun. 18, 2019

(54) METHODS FOR PURIFICATION OF NON-PSYCHOACTIVE ISOPRENOID COMPOUNDS FROM BIOLOGICAL EXTRACTS

(71) Applicants: Bradley Lee Robertson, Sausalito, CA (US); Michael Clemmons, Mill Valley, CA (US)

(72) Inventors: Bradley Lee Robertson, Sausalito, CA (US); Michael Clemmons, Mill Valley, CA (US)

( * ) Notice: Subject to any disclaimer, the term of this patent is extended or adjusted under 35 U.S.C. 154(b) by 0 days.

(21) Appl. No.: 15/095,176

(22) Filed: Apr. 11, 2016

(65) Prior Publication Data

US 2018/0273501 A1    Sep. 27, 2018

(51) Int. Cl.
*C07D 311/80* (2006.01)
*B01D 11/02* (2006.01)
*B01D 9/00* (2006.01)
*B01D 21/26* (2006.01)

(52) U.S. Cl.
CPC .......... *C07D 311/80* (2013.01); *B01D 9/0004* (2013.01); *B01D 9/0018* (2013.01); *B01D 9/0036* (2013.01); *B01D 11/0203* (2013.01); *B01D 11/0292* (2013.01); *B01D 21/262* (2013.01); *B01D 2009/0086* (2013.01); *C07B 2200/13* (2013.01)

(58) Field of Classification Search
CPC ..................................................... C07D 311/80
USPC .......................................................... 549/390
See application file for complete search history.

(56) References Cited

U.S. PATENT DOCUMENTS

2015/0038567 A1    2/2015    Herkenroth et al.

*Primary Examiner* — Taofiq A Solola
(74) *Attorney, Agent, or Firm* — KSIP

(57) ABSTRACT

A method for the extraction and isolation of the terpene and isoprenoid compounds from plant material, followed by a centrifugal force induced selective crystallization of isoprenoids resulting in a separation of terpene and isoprenoid fractions. This this method is suitable for the extraction of cannabinoids from *Cannabis* and the enrichment tetrahydrocannabinolic acid and reduction of tetrahydrocannabinol in an extract. The purity of tetrahydrocannabinolic acid resulting from centrifugal crystallization is such that dissolution and selective recrystallization of tetrahydrocannabinolic acid is possible resulting in >99.9% pure tetrahydrocannabinolic acid, w/w.

17 Claims, 15 Drawing Sheets

| Documented Effect | Study | Literature Reference |
|---|---|---|
| Anti-inflammatory | Evaluation of the cyclooxygenase inhibiting effects of six major cannabinoids isolated from Cannabis sativa | Ruhaak LR, Felth J, Karlsson PC, Rafter JJ, Verpoorte R, Bohlin L. (2011), Biological and Pharmaceutical Bulletin 34 (5): 774-8, doi:10.1248/bpb.34.774, PMID 21532172 |
| Neuroprotective to Oxidative Stress | Effects of cannabinoids Δ(9)-tetrahydrocannabinol, Δ(9)-tetrahydrocannabinolic acid and cannabidiol in MPP(+) affected murine mesencephalic cultures | Moldzio R, Pacher T, Krewenka C, Kranner B, Novak J, Duvigneau JC, Rausch WD. (2012), Phytomedicine 19 (8-9): 819-24, doi:10.1016/j.phymed.2012.04.002, PMID 22571976 |
| Antiemetic (Anti-Vomitting) | The tetrahydrocannabinol and tetrahydrocannabinolic acid content of cannabis products | Baker PB, Taylor BJ, Gough TA. (1981), Journal of Pharmacy and Pharmacology 33 (6): 369-72, doi:10.1111/j.2042-7158.1981.tb13806.x, PMID 6113009 |
| Anti-Prostate Cancer | Non-THC cannabinoids inhibit prostate carcinoma growth in vitro and in vivo: pro-apoptotic effects and underlying mechanisms | De Petrocellis L, Ligresti A., Moriello A.S., Iappelli M., Verde R., Stott C.G., Cristino L., Orlando P., and Di Marzo V. (2013), British Journal of Pharmacology 168 (1): 79-102, doi:10.1111/j.1476-5381.2012.02027.x, PMC 3570006 |
| THCA stability in vivo | Studies on the metabolism of the Delta-9-tetrahydrocannabinol precursor delta-9-tetrahydrocannabinolic acid A (Delta9-THCA-A) in rat using LC-MS/MS, LC-QTOF MS and GC-MS techniques | Jung J, Meyer MR, Maurer HH, Neusüss C, Weinmann W, Auwärter V. (2009), Journal of Mass Spectrometry 44 (10): 1423-33, doi:10.1002/jms.1634, PMID 19728318 |

FIG. 2

| sample | Plant material | | Initial extract | | | centrifugally separated crystals | | | | dissolved-recrystallized | | | |
|---|---|---|---|---|---|---|---|---|---|---|---|---|---|
| | weight | % THCA by weight | weight | % THCA by weight | % yield (extraction) | weight | % THCA by weight | % yield (crystallization) | % yield (overall process) | weight | % THCA by weight | % yield (re-crystallization) | % yield (overall process) |
| Plant Material #1 | 100 g | 17.6% | 12.2 g | 49.9% | 34.2% | 5.9g | 94.5% | 91.6% | 31.3% | 5.4g | 99.97% | 96.8% | 30.3% |

FIG. 5b

METHODS FOR PURIFICATION OF NON-PSYCHOACTIVE ISOPRENOID COMPOUNDS FROM BIOLOGICAL EXTRACTS

CROSS-REFERENCE TO RELATED APPLICATIONS

This application claims the benefit of U.S. Provisional Application Ser. No. 62/146,198 entitled "A Method for Extracting Cannabinoids and Terpenes through Centrifugation", filed Apr. 10, 2015.

FIELD OF THE INVENTION

The present invention relates to a method for the isolation of natural compounds from extracts of complex biological materials. More particularly, the present invention relates to a method suitable for the extraction of terpene and isoprenoid compounds from the female flowers of *Cannabis* species, followed by the isolation of highly purified tetrahydrocannabinolic acid (THCA), with this highly purified tetrahydrocannabinolic acid being suitable for use in medicinal applications, including those in which the psychoactive effects of tetrahydrocannabinol (THC) are undesirable—as THCA has neither the psychoactive effects nor legal prohibitions of THC.

BACKGROUND OF THE INVENTION

In recent years, the use of *Cannabis* and *Cannabis* extracts for medicinal purposes has increased. However, the complex chemical composition of *Cannabis* and *Cannabis* extracts presents several complications for medicinal use. First, while some components of *Cannabis* have medically useful characteristics, other compounds result in the undesirable psychoactive and narcotic effects that limit the medical usefulness of *Cannabis* in many applications and patients. Further, the mixed composition of plant-based materials (which varies due to strain, cultivation method, preparation, or age) makes safety and efficacy testing difficult, as various compounds may have synergistic or interfering effects. In addition, while numerous compounds in *Cannabis* have been shown to have medicinal use, a small number of psychoactive compounds from *Cannabis* are scheduled by the federal government as controlled substances. Without isolated and purified compounds of medicinal value from *Cannabis*, pharmaceutical usage of specific *Cannabis*-derived compounds is greatly limited.

The structures of the isoprenoid compounds THCA (also known as 2-COOH-THC) and THC (L19-THCA) are shown in FIG. 1a and FIG. 1b, respectively. THC is the primary psychoactive compound in *Cannabis*, while THCA is neither psychoactive norfederally scheduled as a controlled substance (Stark, 1990, *Marijuana Chemistry: Genetics, Processing, Potency*). Academic studies have shown that isolated THCA has a number of medically useful characteristics, such as anti-inflammatory properties, anticancer effects, and antiemetic effects. A table of these studies is shown in FIG. 2.

THC is a chemical degradation product of THCA. FIG. 3 shows the reaction by which THCA is decarboxylated and converted to THC (and carbon dioxide). The reaction shown in FIG. 3 is greatly accelerated by heat; while the THCA is the predominant compound in living and freshly harvested *Cannabis*, THC is formed rapidly as *Cannabis* is burned (e.g., by smoking). Small amounts of THC are formed slowly from THCA as *Cannabis* is dried or aged. In addition to heat instability, the degradation of purified THCA to THC is accelerated by ultraviolet light, oxygen, or acidic conditions (Zoller et al., 2000). Notably, THCA is stable in vivo, as shown by mass spectrometry in a study of THCA metabolism in rat by Jung et al., 2009.

Current methods for purification of THCA from THC involve expensive and time intensive methods that do not scale well, such a high-pressure liquid chromatography. While current THCA purification methods are suitable for the production of analytical or research quantities of THCA, medicinal or pharmaceutical production would require a less expensive and more robust process.

There is currently a lack of data available with respect to the effects of various plant-based medicines, remedies or health-promoting agents—even widely used remedies may not have undergone substantial clinical testing. The lack of data is particularly acute with respect to historically controlled substances, such as *Cannabis*. The effects of plant-based products may vary significantly between strains, between preparations, and between delivery routes. The lack of highly purified and stable plant based medicinal compounds is one of the primary impediments to meaningful testing of the medicinal properties of these compounds, or to any pharmaceutical use.

There exists an unmet need to develop a method for the rapid extraction of THCA from *Cannabis*, followed by purification of THCA from THC and other *Cannabis* compounds, psychoactive or otherwise. There further exists an unmet need that this purification method be inexpensive and robust, so as to be suitable to scaled production. There further exists an unmet need for methods by which the purified THCA may be stabilized to prevent subsequent degradation of THCA to THC.

SUMMARY OF THE INVENTION

It is an object of the present invention to provide a method that allows for the extraction of terpene and isoprenoid compounds from the flowers of *Cannabis* species, with the resulting extract then being subject to a fractionation process by which the terpene compounds present in the extract are separated from the isoprenoid compounds, with this isolated isoprenoid fraction containing cannabinoids that are subject to a crystallization step resulting in the selective crystallization of highly-purified tetrahydrocannabinolic acid (THCA).

It is an additional object of the present invention to provide a method that allows exclusion of factors from the preparation and purification of crystalized THCA that result in the degradation of THCA to THC.

It is an additional object of the present invention to provide a method that improves the stability of purified THCA, preventing the degradation of purified THCA to THC.

It is an additional object of the present invention to provide a method that results in the formation of large, periodic (rather than amorphous) crystals of THCA.

Concepts were developed for the extraction of terpene and isoprenoid compounds from *Cannabis* plant material (or *Cannabis* cell culture), with the plant material first being subject to a maceration and then being chilled, with the chilled plant material then being introduced into a pre-chilled solvent extraction chamber, with the plant material and solvent extraction chamber then being degassed, with liquefied and chilled n-propane then being introduced into the degassed solvent extraction chamber containing plant material such that the liquid n-propane solubilizes the terpene and isoprenoid compounds from plant material, with the liquid n-propane containing dissolved plant compounds then being separated from the residual plant material by filtration, with the filtered liquid n-propane containing dissolved plant compounds then being treated such that the n-propane is recovered leaving behind an extract comprised of the compounds solubilized from the plant material, including terpene and isoprenoid compounds. This extract, containing compounds solubilized from the plant material, including terpene and isoprenoid compounds, is then placed on a surface, with this surface then being placed into a temperature controlled chamber, with this temperature controlled chamber then being subject to vacuum, with the temperature and vacuum being such that after a certain period of time polymorphic crystals begin to form, at which point the extract containing the polymorphic crystals is removed from the extraction chamber and placed into a centrifuge, with the extract and polymorphic crystals then being subject to centrifugal separation, with the pelleted polymorphic crystals containing primarily isoprenoid compounds being separated from the terpene compound-rich supernatant, and with the terpene compound-rich supernatant then being filtered to remove residual small isoprenoid crystals.

Concepts were developed for the specific purification of tetrahydrocannabinolic acid (THCA) from the polymorphic isoprenoid crystals by dissolution of the isoprenoid crystals into a nonpolar solvent or semi-polar solvent, followed by controlled, selective crystallization of THCA.

Concepts were further developed for accelerating the crystallization of THCA by the seeding of the solution of dissolved isoprenoid compound crystals in nonpolar solvent with microcrystals of THCA or other suitable microcrystals or fine materials.

Concepts were further developed for the minimization of THCA degradation to THC during the extraction process by the exclusion of oxygen from the extraction system through use of inert gas sparging of systems and solvents, resulting in improved THCA yields.

Concepts were further developed for the minimization of THCA degradation to THC during the extraction process by reducing the oxidative potential in the solvent and system through inclusion of reducing agents in the process, resulting in improved THCA yields.

Concepts were further developed for the minimization of THCA degradation to THC during the extraction process by regulating the pH or acid/base conditions in the solvent and system through inclusion of buffering agents in the process, resulting in improved THCA yields.

Concepts were further developed for the minimization of THCA degradation to THC during the extraction process by reducing the oxidative potential in the solvent and system through inclusion gas scrubbing and solvent treatment processes, resulting in improved THCA yields.

Concepts were further developed for the accelerating the crystallization of THCA by the seeding of the solution of dissolved isoprenoid compound crystals with cationic compounds, including both cationic salts and cationic liquids.

Concepts were further developed for stabilizing the purified THCA through saponification of THCA to THCA conjugate salts though reaction of THCA with base, followed by crystallization of THCA conjugate salts.

Concepts were further developed for stabilizing the purified THCA by coating the THCA crystals with a material that excludes oxygen and/or ultraviolet light.

BRIEF DESCRIPTION OF THE FIGURES

FIG. 2 is a table showing academic studies that have shown medicinal effects of THCA, and the stability of THCA in vivo.

FIG. 5b is a table showing one example of primary embodiment, with this table presenting data on the enrichment of THCA from plant biomass to enriched extract through use of the primary embodiment of this invention, with THCA values shown having been measured by mass spectrometry (MS) following separation by high pressure liquid chromatography.

DETAILED DESCRIPTION OF THE INVENTION

Figure 4A:
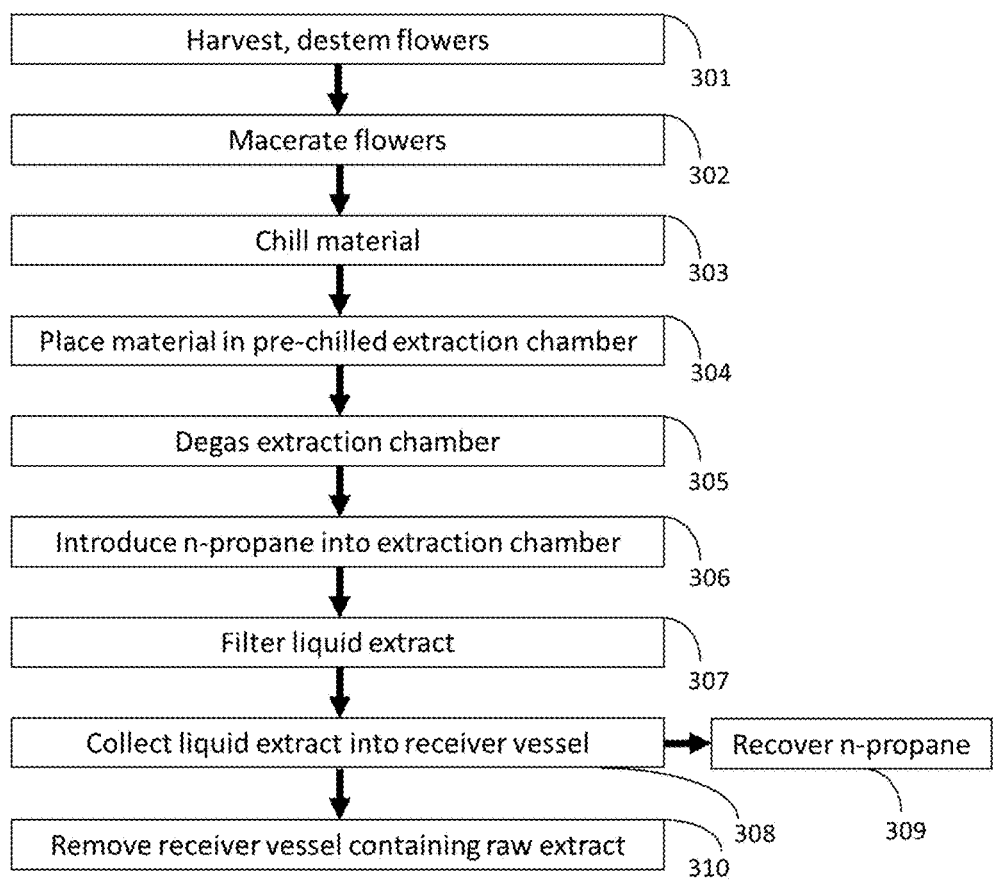
FIG. 4a is a box diagram showing the pre-fractionation extraction process by which terpene and isoprenoid compounds are extracted from *Cannabis*, similar to that shown in the primary embodiment of U.S. Provisional Application Ser. No. 62/146,198.
Figure 4B:
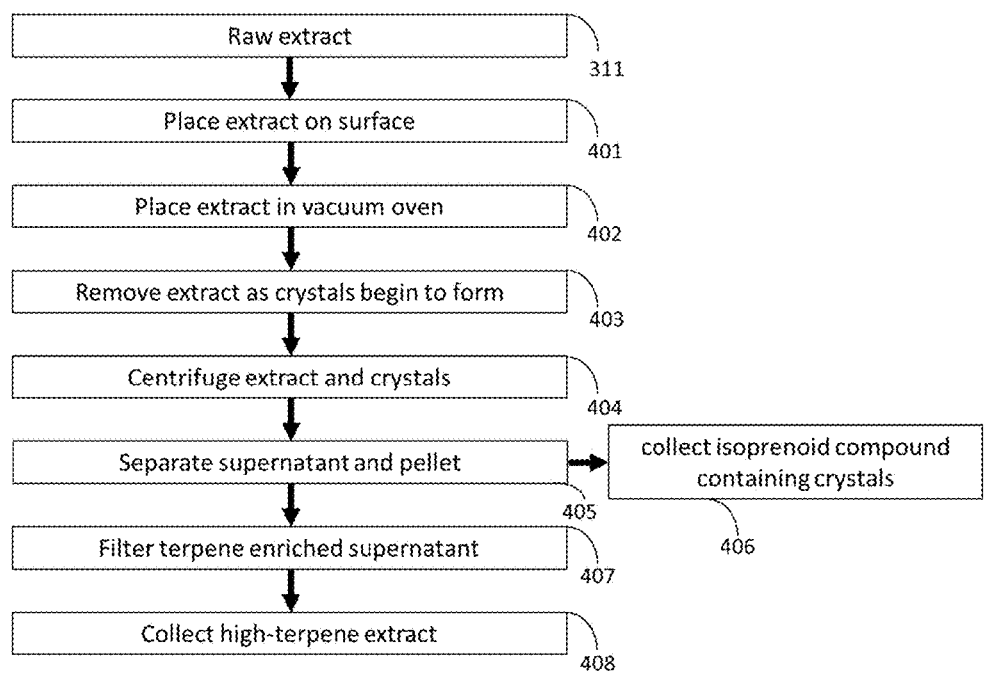
FIG. 4b is a box diagram showing the post-extraction fractionation process by which isoprenoid and terpene compounds are separated from *Cannabis* extracts, similar to that shown in the primary embodiment of U.S. Provisional Application Ser. No. 62/146,198.

With reference to FIG. 4a and FIG. 4b, the initial purification of isoprenoid compounds from *Cannabis* is conducted similarly to the process previously described in U.S. Provisional Application Ser. No. 62/146,198 entitled "A Method for Extracting Cannabinoids and Terpenes through Centrifugation", filed Apr. 10, 2015. FIG. 4a shows a flow chart representing the initial extraction process by which THCA, as well as other cannabanoids, isoprenoids, and terpenes are extracted from *Cannabis*. In 301, the female flowers of *Cannabis* are harvested and destemmed. In 302 the destemmed flowers from 301 are shredded, macerated, ground, milled, or otherwise reduced in size. In 303, the macerated flower material from 302 is chilled. In 304, the chilled flower material from 303 is placed into a pre-chilled extraction chamber. In 305, the extraction chamber is sealed and degassed. In 306, supercritical (liquid) n-propane is introduced into the degassed extraction chamber from 305, with this n-propane dissolving and extracting chemical compounds from the flower material. In 307, the liquid n-propane containing dissolved compounds extracted from the flower material from 306 is separated from the flower material solids by filtration. In 308, the filtered liquid n-propane containing dissolved compounds extracted from the flower material from 307 is collected into a receiver vessel. In 309, the n-propane is removed from the extract contained in the receiver vessel in 308. In 310, the extract-containing receiver vessel, from which n-propane had been recovered in 309, is removed from the extraction chamber apparatus, and this raw extract is ready for further fractionation.

In some embodiments, the flowers are not dried. In one preferred embodiment, the flowers are reduced in size to 1-3 mm. In some embodiments, the flowers are not reduced in size. In one preferred embodiment, the flowers are chilled to between 0° C. and −100° C. prior to extraction. In one preferred embodiment, the extraction chamber is pre-chilled to between 0° C. and −100° C. In one preferred embodiment, the n-propane is pre-chilled to between 0° C. and −100° C. before introduction into the extraction chamber. In some embodiments, there is a soak time upon introduction of the n-propane into the extraction chamber prior to separating the n-propane containing dissolved compounds from the plant material. In other embodiments there is no soak time, and separation of the n-propane containing dissolved compounds from the plant material is immediate. In some embodiments, the n-propane is recovered from the receiver vessel by use of differential pressure or temperature such that the n-propane becomes a gas and is readily removable, as is known in the art.

FIG. 4b shows a flow chart representing an initial THCA purification step following the extraction process from U.S. Provisional Application Ser. No. 62/146,198 entitled "A Method for Extracting Cannabinoids and Terpenes through Centrifugation", filed Apr. 10, 2015. In 311, the raw extract removed from the receiver vessel 310 (from FIG. 4a) it taken for fractionation. In 401, the raw extract from 311 is placed on a surface. In 402, the raw extract on a surface from 401 is placed in a vacuum oven, with this oven then being closed and purged of air. The extract is incubated in the vacuum oven until polymorphic crystals begin to form, at which point it is removed, 403. In 404, the extract removed from the vacuum oven containing polymorphic crystals from 403 is placed into a temperature controlled centrifuge, with the centrifuge then being activated so as to separate the solid crystals from the liquid phase of the extract. In 405, the centrifugally pelleted crystal fraction and liquid supernatant fraction from 404 are separated. In 406, the crystals from 405, which contain isoprenoid compounds crystals, are collected. In 407, the liquid supernatant fraction from 405, which is rich in terpenes, is filtered to remove any residual crystals. In 408, the filtered terpene-rich extract from 407 is recovered.

In some embodiments, the process may further comprise steps of filtering the condensate during centrifugation to collect water insoluble material and extracting the insoluble material. In some embodiments, precipitants are added to the extract, in order to affect the precipitation of impurities, which will then be subsequently filtered out. In some embodiments, precipitants are added to the extract in order to affect the selective precipitation of target cannabinoid compounds, with subsequent centrifugation or filtration being used to harvest these target compounds. In one preferred embodiment, sucrose crystals (sugar) can be used as a selective precipitant for THCA relative to other cannabinoids found in a non-polar solvent extract of cannabinoids—with this selectivity owing to the hydrophilic nature of sucrose and the relatively greater hydrophilic nature of THCA to other cannabinoids (resulting from the carboxylic acid moiety on THCA).

Figure 5A:
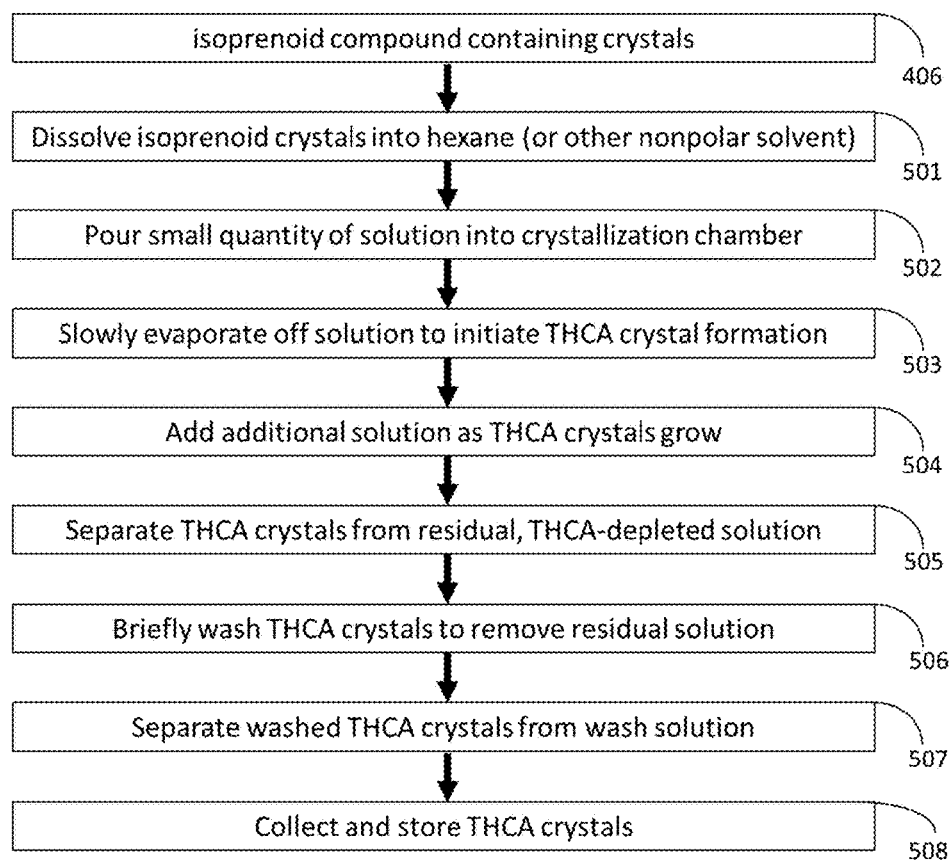
FIG. 5a is a box diagram showing the primary embodiment of this invention.

The primary embodiment of this invention is shown in FIG. 5a. In 501, isoprenoid compound crystals from 406 are dissolved into hexane. In 502, a portion of the hexane solution of dissolved compounds is poured into a crystallization chamber. In 503, a portion of the hexane or other solvent is evaporated while maintaining low temperature, by methods including but not limited to pulling a vacuum or blowing dry nitrogen gas on the solution. In 504, additional hexane solution containing dissolved compounds is added to the crystallization chamber as THCA crystals form and/or as solvent is evaporated. In 505, THCA crystals are removed from the residual THCA-depleted solution. In 506, THCA crystals are briefly washed in a small volume of nonpolar solvent to remove residual THCA-depleted solution and any contamination compounds that may have adsorbed to the external surface of the THCA crystals. In 507, washed THCA crystals are separated from the wash solution. In 508, THCA crystals are collected and stored. In some embodiments, crystals are stored under inert gas and/or in UV resistant containers, such as packaging THCA crystals in argon filled amber glass ampules. In some embodiments, a nonpolar solvent other than hexane is used, such as pentane, heptane, butane, ether, or any of a host of other solvents known in the art, or mixtures of specific solvents. In some embodiments, the initial THCA containing material is extracted and somewhat purified by a method other than that described in FIG. 4a and FIG. 4b, though we note that unless the initial THCA purity level is rather high (>90% THCA), subsequent re-crystallization of THCA may be impossible or impractically slow.

In some embodiments, the organic solvents used for recrystallization may include but are not limited to butane, propane, ethyl acetate, heptanes, toluene, ethanol, methanol, isopropanol and combinations thereof. In certain advantageous embodiments the target compound(s)/solvent mixtures temperature is brought to between −10 Celsius and −70 Celsius and precipitates are filtered out. In certain advantageous embodiments the organic solvent comprises ethyl acetate. In these and other embodiments it may also be preferable to adjust pH of the extract/solvent mixture to enhance precipitation of at least one target compound(s).

Figure 1A:
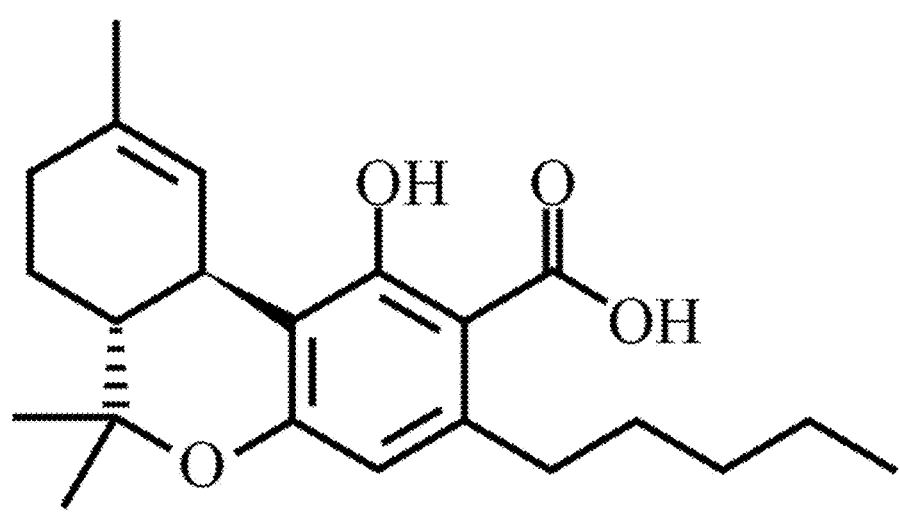
FIG. 1a shows the chemical structure of the non-psychoactive compound tetrahydrocannabinolic acid (THCA).
Figure 1B:
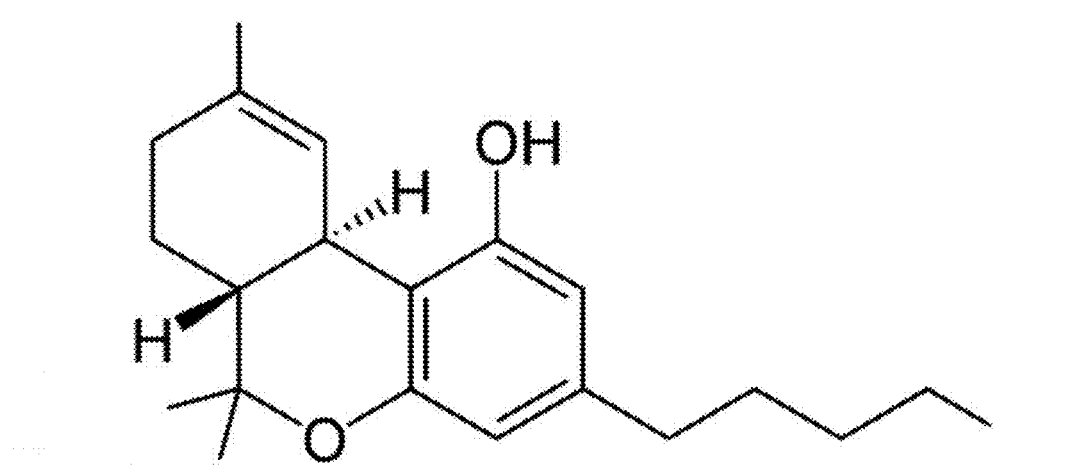
FIG. 1b shows the chemical structure of tetrahydrocannabinol (THC).
Figure 3:
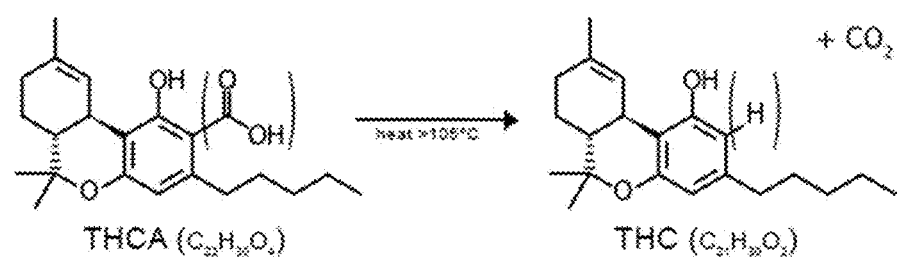
FIG. 3 shows the decarboxylation reaction by which TCHA is degraded into THC.

As an example of the primary embodiment, consider the preparation of a highly pure THCA *Cannabis* extract meant for use in research into the potential treatment of a human disease state, such as prostate cancer or various inflammatory diseases. (THCA has been indicated as potentially useful in treating these disease states, as in known in the art, with some examples being shown in FIG. 3.) While medicinal benefits have been shown for THCA, the narcotic effects of delta-9 THC and sedative effects cannabidiol (CBD) are undesirable in medicinal applications. Through use of the method of the primary embodiment, the purity of THCA from a sample of *Cannabis* can be greatly increased, possibly to within specifications for pharmaceutical usage (>99.9% purity) with an effective elimination of delta-9 THC and CBD, with this material having no intoxicating effect on the patient being treated. An example of the enrichment of THCA through use of the method of the primary embodiment is shown as a table in FIG. 5b. Briefly, 100 g of dried, mature *Cannabis* flower, with an initial THCA content of 17.8% w/w, subject to extraction by the method of U.S. Provisional Application Ser. No. 62/146,198 using subcritical n-propane as a solvent, with the initial extract having 49.5% THCA w/w, and the centrifugally separated crystals being 94.5% THCA w/w. Through use of the primary embodiment of this invention the purity of THCA in the re-crystalized material was increased to 99.97% with only limited THCA yield loss relative to the centrifugally separated crystals (30.3% and 31.3% yield, respectively, as shown in FIG. 5b). THCA analysis was done using an AGILENT 1100 (Agilent, Santa Clara, Calif.) HPLC with G1946D mass spectrometry detector using methods known in the art of liquid chromatography coupled mass spectrometry.

Figure 6:
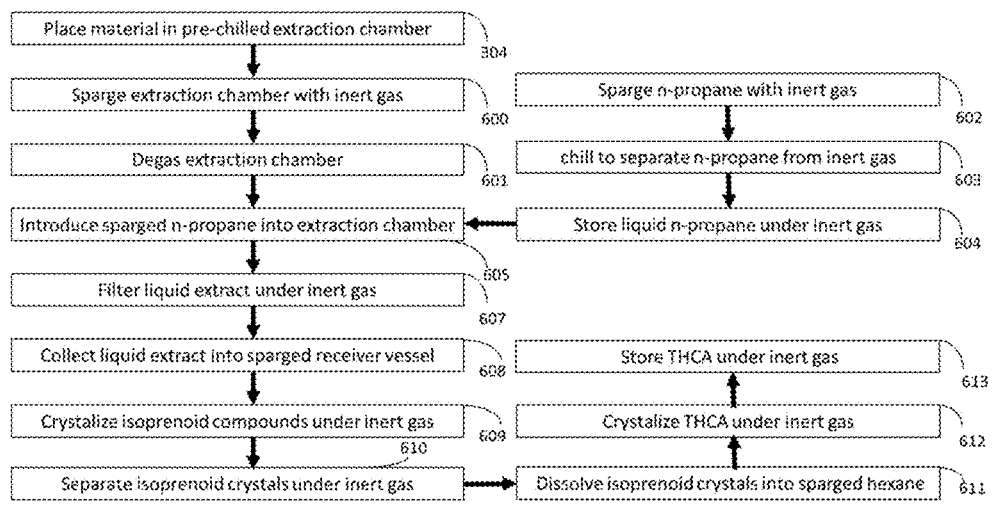
FIG. 6 is a box diagram showing the second embodiment of this invention.

The second embodiment of this invention is shown in FIG. 6, in which the extraction and crystallization process of material from *Cannabis* takes place in chambers and solvents that are sparged with inert gas in order to remove oxygen from the process and prevent the degradation of THCA to THC. Destemmed, macerated *Cannabis* is placed in the extraction chamber in 304. Inert gas is then applied to the extraction chamber in 600, and this inert gas is subsequently removed by vacuum degassing in 601. In 602, inert gas is bubbled through liquefied n-propane. In 603, the liquid n-propane is separated from the headspace gas (including both sparge gas and any gas driven from the liquid n-propane, including H2S, 02, or CO2). In 604, the sparged n-propane is stored under inert gas. In 605, the sparged n-propane from 604 is applied to the degassed extraction chamber and macerated *Cannabis* from 601. In 607, the *Cannabis* extract in liquid n-propane is filtered from the residual plant material under inert gas. In 608, the filtered extract is placed into an inert gas sparged collection vessel. In 609, the initial crystallization of isoprenoid compounds, including centrifugation as previously described in this application, takes place under inert gas. In 610, isoprenoid compound crystals are separated under inert gas. In 611, isoprenoid compound crystals are dissolved into inert gas sparged hexane. In 612, THCA crystals are formed under inert gas. In 613, THCA crystals are stored under inert gas. In some embodiments, the inert gas is argon, nitrogen, or other inert gas known in the art.

As an example of the second embodiment of this invention, consider the extraction of THCA from *Cannabis* as an initial step in pharmaceutical production. As THCA is degraded to THC by oxygen, the removal of oxygen from the system by inert gas sparging increases the final THCA yield. As THCA is degraded by acid, the removal of H2S and CO2, both of which result in acid formation with dissolution in water (the small amount of water in biomass absorbs these gases, particularly at low temperatures), results in improved THCA yield. In addition to improving yield, in some applications, even trace THC contamination is restrictive. Through use of the second embodiment of this invention, THCA yield is increased and THC contamination is avoided.

Figure 7:
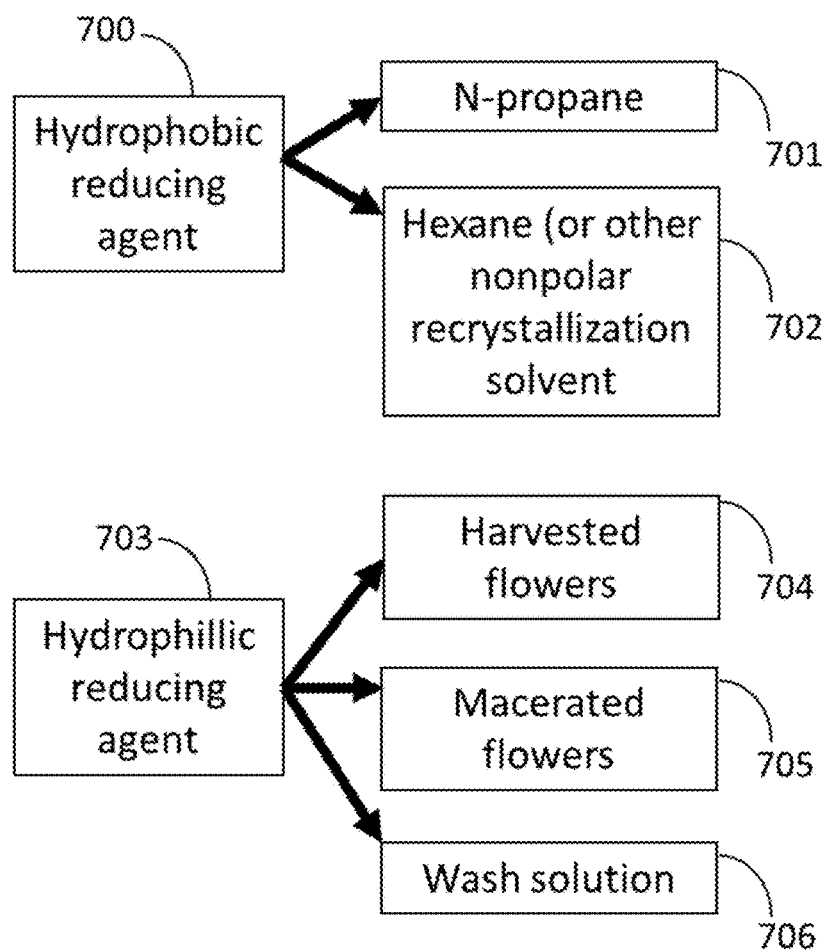
FIG. 7 is a box diagram showing the third embodiment of this invention.

The third embodiment of this invention is shown in FIG. 7, in which reducing agents are added to various points in the extraction and crystallization process to prevent THCA oxidation to THC by removal of dissolved oxygen from solvents or systems. Hydrophobic reducing agents, 700, can be added to n-propane, 701, or hexane (or other nonpolar re-crystallization solvent), 702. Hydrophilic reducing agent, 703, can be added to harvested *Cannabis* flowers 704, macerated flowers, 705, or crystal wash solution, 706. Hydrophobic and hydrophilic reducing agents of various compositions are known in the art.

As an example of the third embodiment of this invention, consider the extraction of THCA from *Cannabis* as an initial step in pharmaceutical production. As THCA is degraded to THC by oxygen, the removal of dissolved oxygen from the system by use of reducing agents (that react with dissolved oxygen and oxygen species) increases the final THCA yield. Through use of the third embodiment of this invention, and introducing reducing agents into one or more steps in the process, THCA yield is increased and THC contamination is eliminated.

Figure 8:
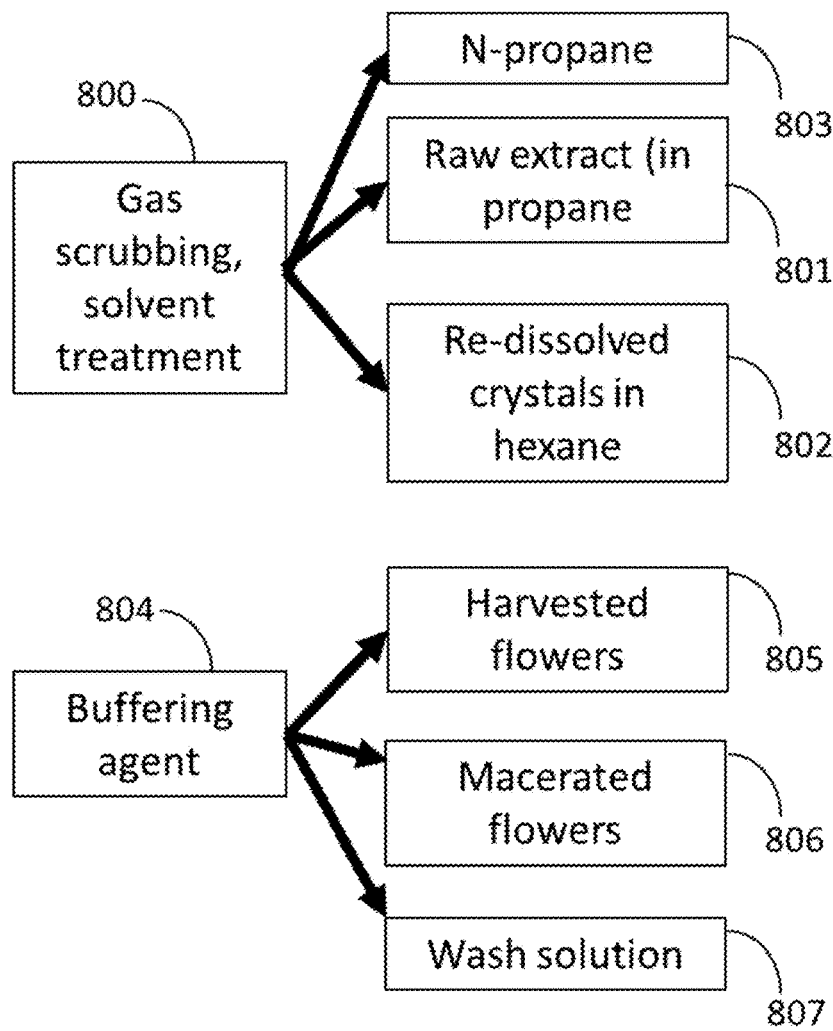
FIG. 8 is a box diagram showing the fourth embodiment of this invention.

The fourth embodiment of this invention is shown in FIG. 8, in which buffering, basic, or pH regulating compounds are integrated into the process in order to minimize the degradation of THCA. In 800, pH regulating agents are introduced into the nonpolar elements of the system in order to remove acid or acid-forming gasses (i.e., CO2 or H2S), with these compounds from 800 being used for solvent treatment or gas scrubbing of n-propane, 803, n-propane extracts of *Cannabis*, 801, or re-dissolved THCA crystals in hexane, 802. In 804, pH buffering agents that are water soluble are added to harvested flowers, 805, macerated flowers, 806, or crystal wash solution, 807. In some embodiments, the nonpolar solvents or gasses are treated with bases or gas scrubbing agents known in the art. In some embodiments, the pH buffering agents include any of the organic or inorganic pH buffering agents known in the art.

As an example of the fourth embodiment of this invention, consider the extraction of THCA from *Cannabis* as an initial step in pharmaceutical production. As THCA is degraded to THC by acid, the removal of dissolved acidic compounds or acid-forming gasses from the system by use of base or pH buffering agents increases the final THCA yield. Through use of the fourth embodiment of this invention, and introducing pH regulating or acid removing compounds into one or more steps in the process, THCA yield is increased and THC contamination is eliminated.

Figure 9:
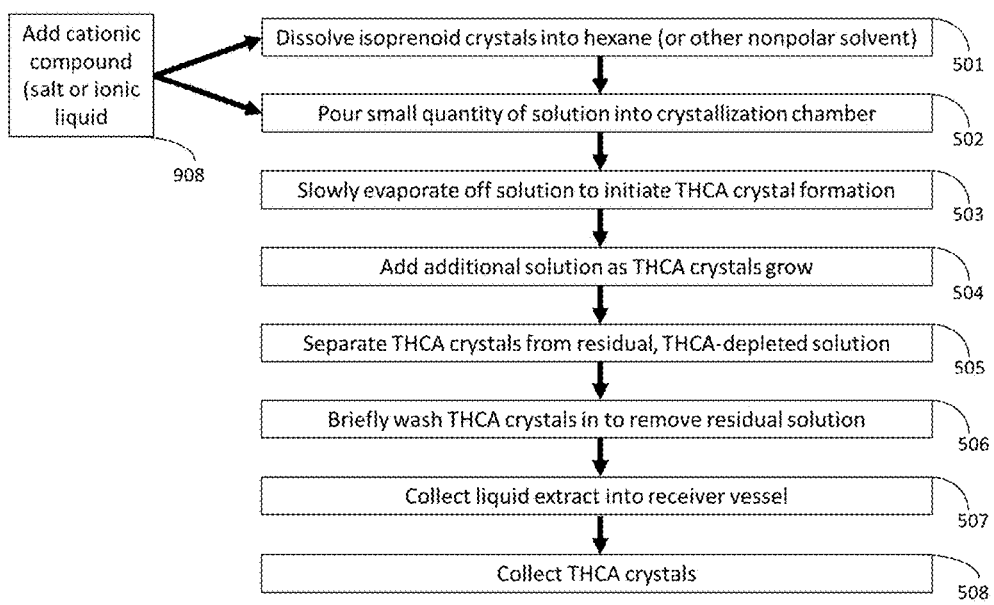
FIG. 9 is a box diagram showing the fifth embodiment of this invention.

The fifth embodiment of this invention is shown in FIG. 9, in which cationic compounds are added to initiate or accelerate the crystallization of THCA from nonpolar solvent. Cationic compounds, 908, can be introduced into the hexane solution of dissolved isoprenoid compounds, 501, or into the crystallization chamber, 502. In some embodiments, the cations are introduced as salts. In some embodiments, cations are introduced as ionic liquids. In some embodiments, the cation is monovalent. In some embodiments, the cationic compound is multivalent.

As an example of the fifth embodiment of this invention, consider the industrial purification of THCA from extract. By making use of the fifth embodiment of this invention, the rate of crystallization can be increased, reducing labor usage as well as allowing for less installed tank/infrastructure per unit product.

Figure 10A:
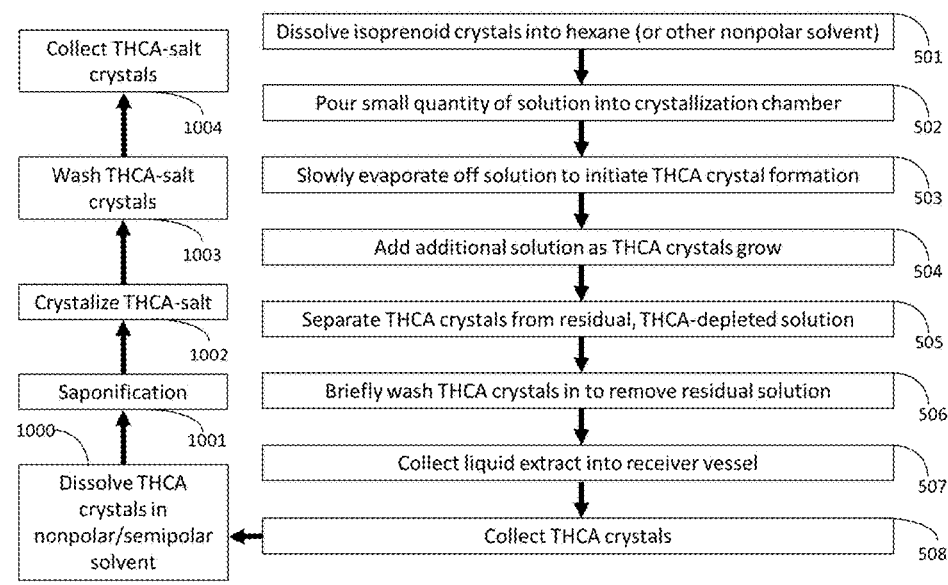
FIG. 10a is a box diagram showing the sixth embodiment of this invention.
Figure 10B:
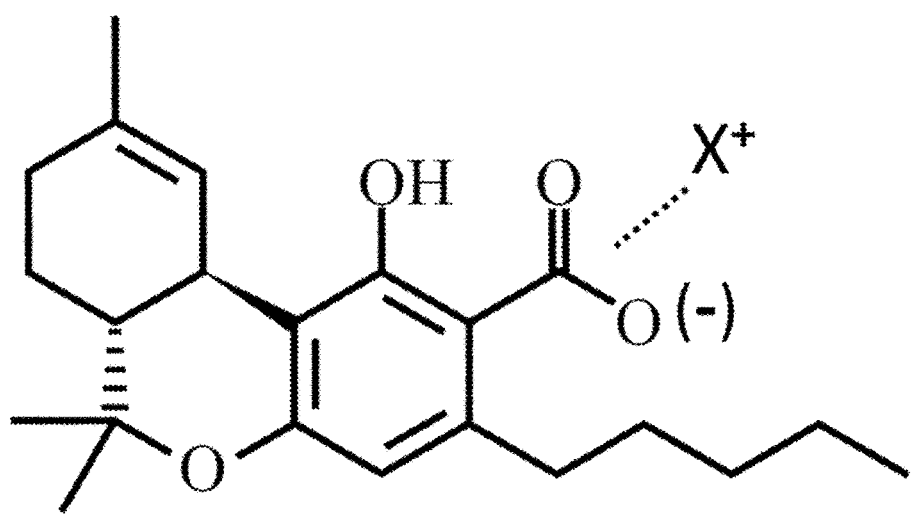
FIG. 10b shows the chemical structure of THCA salts formed in the sixth embodiment of this invention, with $x^+$ preferably being from the group consisting of NH/, mono-, di- or trivalent metal ions, and primary, secondary, tertiary or quaternary organic ammonium ions with up to 48 C atoms, which may bear still further functional groups.

The sixth embodiment of this invention is shown in FIG. 10a and FIG. 10b, in which the recrystallized THCA is reacted with base to form a THCA salt, with this THCA salt being of improved stability relative to THCA. Regarding FIG. 10a, in 1000, THCA crystals from 508 are re-dissolved into a solvent, such as an intermediate chain alcohol solution (e.g., 95% isopropanol). In 1001, base is then added to this semipolar solvent solution under controlled conditions in order to saponify the dissolved THCA. In 1002, the THCA-salt is crystallized and separated from the solvent and base. In 1003, the THCA-salt crystals are washed to remove any residual solvent and base. In 1004, THCA-salt crystals are collected and store. Regarding FIG. 10b, the general structure for a THCA-salt is shown, with X being the cation conjugate ion from the base. Suitable bases for the formation of crystalline salts are primary, secondary and tertiary organic amines with up to 48 carbon atoms such as dicyclohexylamine, ammonia, alkoxides, hydroxides, carbonates, hydrogen carbonates, carboxylates and other basic salts of elements of the first, second and third main group and of tin, lead and bismuth, and the alkoxides, hydroxides, carbonates, hydrogen carbonates, carboxylates and other basic salts of transition elements such as silver (Ag+). Inorganic salts may be complexed (e.g. silver hydroxide as silver diammine complex) in order to increase the solubility. Further suitable organic bases are pharmaceutical active substances with at least one basic nitrogen atom in the molecule, such as morphine, hydromorphone (Palladon®), buprenorphine, etc. Suitable solvents depend on the base used, including semipolar solvents such as 95% isopropanol (5% water) and nonpolar solvents such as hexane, or other solvents known in the art suitable for saponification, including alcohols, esters, ethers, ketones, hydrocarbons, halogenated hydrocarbons and nitriles with up to 20 carbon atoms.

As an example of the sixth embodiment of this invention, consider the production of THCA for pharmaceutical usage in which the stability of THCA (and lack of THC contamination) is vital. Formation of a salt is widely utilized in the pharmaceutical industry as a way to impart stability to a compound. Through use of the sixth embodiment of this invention, THCA is stabilized to a THCA-salt. Saponification of cannabinoids from *Cannabis* has been previously shown in US 20150038567, however, prior methods resulted in mixed cannabinoid preparations including other cannabinoids, such as cannabidiol (CBD), which have different pharmacological effects than THCA and are undesirable in certain applications. In this invention, THCA is first purified from other isoprenoid compounds, including cannabinoids compounds such as CBD, prior to saponification of THCA to a salt.

Figure 11:
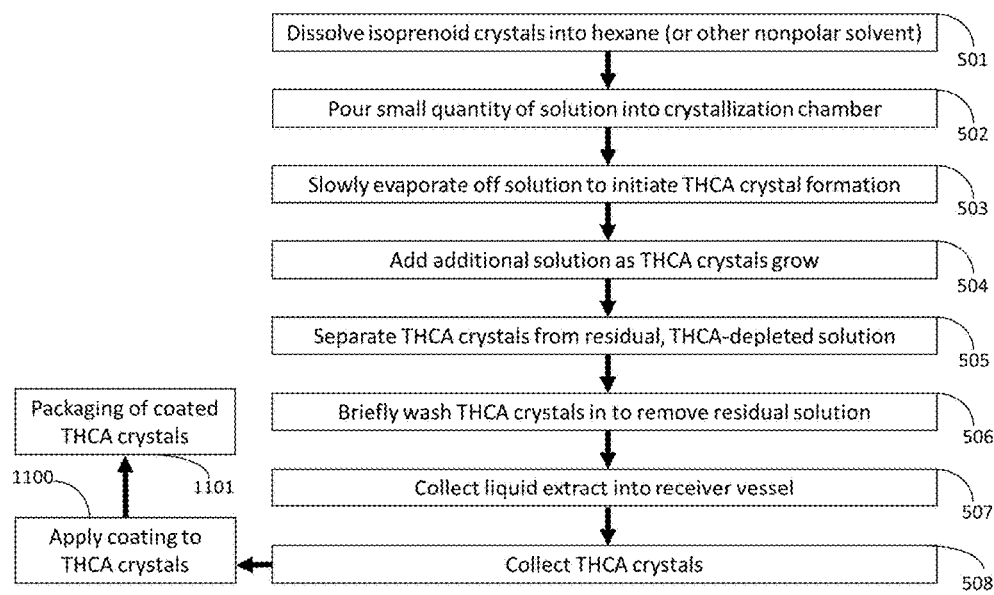
FIG. 11 is a box diagram showing the seventh embodiment of this invention.

The seventh embodiment of this invention is shown in FIG. 11, in which THCA crystals, 508, are coated with a material that is impermeable to water and acts as a barrier to UV light, 1100, prior to the packaging of the THCA crystals for storage or subsequent pharmaceutical use, 1101. In some embodiments, this coating is sprayed or tumbled onto crystals or compressed masses of crystals as seen in the pharmaceutical industry. In some embodiments, this coating is any of a plurality of compositions known in the art.

As an example of the seventh embodiment of this invention, consider THCA crystals being prepared for storage transit from an extraction facility to a pharmaceutical production facility. Through use of the seventh embodiment, the THCA could be stabilized in such a form as to allow this transportation without degradation of the THCA by air or UV light during transit and handling.

In some embodiments, the various embodiments can be combined. For example, extraction and recrystallization could take place under inert gas, and the final THCA crystals produced under inert gas could be coated with an impermeable layer.

Although described with reference to preferred embodiments of the invention, it should be recognized that various changes and/or modifications of the invention can be made without departing from the spirit and scope of the invention. In any case, the invention is only intended to be limited by the scope of the following claims.

The invention claimed is:
1. A method of extracting terpene and isoprenoid compounds from plant material and for selectively enriching the concentration of isoprenoid compounds in a fraction of this extract comprising the steps of:
   a. placing *cannabis* plant material into an extraction chamber;
   b. degassing the extraction chamber;
   c. introducing chilled extraction solvent into the extraction chamber;
   d. filtration of the extract-laden extraction solvent;
   e. removal of the extract-laden extraction solvent from the extraction chamber;
   f. placing the extract-laden extraction solvent into a centrifuge vessel;
   g. centrifuging the centrifuge vessel to promote formation of THCA-laden crystals via recrystallization and to separate the THCA-laden crystals from a supernatant solvent; and
   h. collecting the THCA-laden crystals;
      wherein the extraction solvent is one of subcritical n-propane, butane, hexane, pentane, ether, ethyl acetate, heptane, toluene, naphtha, methanol, ethanol, isopropanol, butanol, or combinations thereof; or,
      wherein the extraction solvent is supercritical carbon dioxide.

2. The method of claim 1 wherein at least one extract of *Cannabis* is substituted for the plant material.

3. The method of claim 1 further comprising the step of:
   addition of sugar, salt, or other precipitants to the extract-laden extraction solvent prior to centrifugation.

4. The method of claim 1 further comprising the step of:
   collection of a terpene rich fraction.

5. A method of increasing the purity of THCA in partially purified THCA-laden material comprising the steps of:
   a. dissolving THCA-laden material into a first volume of solvent so as to form a first volume of solvent with dissolved THCA-laden material;
   b. transferring a first portion of said first volume of solvent with dissolved THCA-laden material into a recrystallization container;
   c. initiating THCA recrystallization;
   d. adding of a second portion of said first volume of solvent with dissolved THCA-laden material into the recrystallization container as THCA crystals form;
   e. separating THCA crystals from said first volume of solvent; and
   f. collecting the separated THCA crystals;
   wherein the first volume of solvent is one of n-propane, butane, hexane, pentane, ether, ethyl acetate, heptane, toluene, naphtha, methanol, ethanol, isopropanol, butanol, or combinations thereof; or,
   wherein the first volume of solvent is supercritical carbon dioxide.

6. The method of claim 5 further comprising the step of:
   addition of acid, base, or buffering compounds to the first volume of solvent or to the first volume of solvent with dissolved THCA-laden material so as to regulate the pH of the system and to promote differential recrystallization.

7. The method of claim 5 wherein recrystallization is initiated by evaporating off some solvent.

8. The method of claim 5 wherein recrystallization is initiated by reducing the temperature of the system.

9. The method of claim 5 wherein recrystallization is initiated by seeding with sugar or cationic salts, cationic liquids, or THCA crystals.

10. The method of claim 5
    wherein THCA crystals are washed with crystal with a second volume of solvent prior to collection, in such a manner as to remove impurities left in residual first volume of solvent used in initial dissolution of the partially purified THCA-laden material;

the second volume of solvent comprising:
propane, butane, pentane, hexane, heptane, toluene or ethyl acetate.

11. The method of claim 1 further comprising the step of:
inert gas sparged into the extraction chamber, collection vessel, or centrifuge vessel prior to solvent extraction of the plant material so as to minimize oxidation of THCA.

12. The method of claim 5 further comprising the step of:
dissolution of partially purified THCA material into said first volume of solvent taking place under inert gas,
and with inert gas sparged first volume of solvent, and the recrystallization of THCA taking place under inert gas.

13. The method of claim 1 further comprising the step of:
addition of pH buffering agent to the plant material prior to extraction so as to minimize oxidation of THCA.

14. The method of claim 5 further comprising the step of:
saponification of separated THCA.

15. The method of claim 14 further comprising the step of:
recrystallization of the THCA salt.

16. The method of claim 5 further comprising the step of:
application of a coating to the THCA crystals.

17. The method of claim 16 wherein said coating is oxygen impermeable.

* * * * *